(12) United States Patent
Sprenger et al.

(10) Patent No.: US 8,771,780 B2
(45) Date of Patent: *Jul. 8, 2014

(54) OLIGOSACCHARIDE INGREDIENT

(75) Inventors: Norbert Sprenger, Savigny (CH);
Rafael Berrocal, Saint-Legier (CH);
Marie-Claire Fichot, Blonay (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/203,867

(22) PCT Filed: Mar. 4, 2009

(86) PCT No.: PCT/EP2009/052551
§ 371 (c)(1),
(2), (4) Date: Aug. 30, 2011

(87) PCT Pub. No.: WO2010/099821
PCT Pub. Date: Sep. 10, 2010

(65) Prior Publication Data
US 2012/0045566 A1 Feb. 23, 2012

(51) Int. Cl.
*A23C 9/00* (2006.01)

(52) U.S. Cl.
USPC .......................................... 426/580; 426/656

(58) Field of Classification Search
None
See application file for complete search history.

(56) References Cited

U.S. PATENT DOCUMENTS

| | | | | |
|---|---|---|---|---|
| 6,323,008 | B1 * | 11/2001 | Pelletier et al. | 435/84 |
| 8,617,631 | B2 * | 12/2013 | Berrocal et al. | 426/580 |
| 2005/0096263 | A1 * | 5/2005 | Keay et al. | 514/8 |
| 2005/0096295 | A1 * | 5/2005 | McMahon et al. | 514/54 |
| 2008/0096794 | A1 * | 4/2008 | Boehm et al. | 514/2 |

FOREIGN PATENT DOCUMENTS

| EP | 2 096 115 | | 2/2009 |
|---|---|---|---|
| JP | 62143697 | A * | 6/1987 |
| RU | 2010139513 | | 10/2012 |
| WO | 2005/016248 | | 2/2005 |
| WO | 2009106528 | | 9/2009 |
| WO | 2010099821 | | 9/2010 |

OTHER PUBLICATIONS

M. H. Abd El-Salam, S. El-Shibiny & W. Buchheim Characteristics and Potential Uses of the Casein Macropeptide.Int. Dairy Journal 6 (1996) 327 341.*
Ola Blixt, Kirk Allin, Laura Pereira, Arun Datta, and James C. Paulson Efficient Chemoenzymatic Synthesis of O-Linked Sialyl Oligosaccharides.J. Am. Chem. Soc. 9 vol. 124, No. 20, 2002.*
Chin-Fen Teo et at.; "Synthesis of Siatyt Tn Glycopeptides—Enzymatic Siatytation by a 2,6-Sialyltransferase from *Photobacterium damseta*", XP-002496043—Adv. Synth. Catat, 2005—347, 967-972.*
Danica P. Galonic et al.; "Oligosaccharide-Peptide Ligation of Glycosyl Thiolates with Dehydropeptides: Synthesis of S-Linked Mucin-Related Glycopeptide Conjugates", XP-002496045—Chem. Eur. J. 2003, 9: 5997-6006.
Bjorn Neubacher et al.; "Preparation of sialylated oligosaccharides employing recombinant trans-sialidase from *Trypanosoma cruzi*", XP-002496044—Orig. Biomal. Chem. 2005—3, 1551-1556.
Chin-Fen Teo et al.; "Synthesis of Sialyl Tn Glycopeptides—Enzymatic Sialylation by a 2,6-Sialyltransferase from *Photobacterium damsela*", XP-002496043—Adv. Synth. Catal, 2005—347, 967-972.
Hiroyuki Iijima et al.; "Synthesis of the N-Terminal Glycopentapeptides of Human Glycophorin Am and an Carrying Trimeric Sialosyl Tn Epitope", XP-002496046—Tetrahedron Letters, vol. 33, No. 51, pp. 7907-7910—1992.

* cited by examiner

*Primary Examiner* — Humera Sheikh
*Assistant Examiner* — Subbalakshmi Prakash
(74) *Attorney, Agent, or Firm* — K&L Gates LLP

(57) ABSTRACT

An oligosaccharide ingredient comprising glycosylated amino acids and peptides of the general formula RnSacm where R is an amino acid residue, Sac is a monosaccharide selected from the group comprising N-acetyl-neuraminic acid, N-acetyl galactosamine and galactose, n has a value between 1 and 10 with the proviso that if n has the value 1 R is a threonine residue or a serine residue and if n has a value between 2 and 10 the peptide contains at least one threonine or serine residue, m has a value between 2 and 4 and at least 20 mol % of the ingredient is N-acetyl-neuraminic acid.

8 Claims, No Drawings

OLIGOSACCHARIDE INGREDIENT

FIELD OF THE INVENTION

The invention relates to an oligosaccharide ingredient rich in sialic acid, food products comprising said oligosaccharide ingredient and processes for producing said oligosaccharide ingredient.

BACKGROUND OF THE INVENTION

Human milk is known to contain a large amount of indigestible oligosaccharides. In fact, indigestible oligosaccharides represent the third largest solid component (after lactose and lipids) in breast milk, occurring at a concentration of 12-15 g/l in colostrum and 5-8 g/l in mature milk. Human milk oligosaccharides are very resistant to enzymatic hydrolysis, indicating that these oligosaccharides may display essential functions not directly related to their calorific value.

Over the past two decades, the chemical structures of human milk oligosaccharides have been studied using NMR spectroscopy and mass spectrometry. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid (when present) occupies the terminal position at the non-reducing end.

The large quantity of sialylated oligosaccharides in human milk is of particular interest. Sialic acid is a nine-C sugar that is a vital structural and functional component of brain gangliosides. It is thought to play an essential role in nerve cell transmission, memory formation and cell to cell communication. Studies in rat pups indicate that early supplementation with sialic acid improves both brain ganglioside sialic acid and learning ability in well-nourished and malnourished animals and that these changes persist into adulthood.

Mother's milk is recommended for all infants. However, in some cases breast feeding is inadequate or unsuccessful for medical reasons or the mother chooses not to breast feed. Infant formulas have been developed for these situations. However, bovine milk which is usually used as the basis of commercially available infant formulas has a much lower content of sialylated oligosaccharides than human milk. As the structure of human milk and the functions of the individual components thereof becomes better understood, it has become apparent that it may be desirable to improve the sialic acid content of infant formulas based on bovine milk.

There are several known sources of sialic acid including free N-acetylneuraminic acid, sialyllactose and other sialylated oligosaccharides, sialic-acid containing gangliosides, and the peptide caseinoglycomacropeptide. Caseinoglycomacropeptide or CGMP is a large carbohydrate-rich, hydrophilic peptide which is the C-terminal moiety of κ casein from which it may be cleaved by enzymatic or acid treatment. In United States Patent Application No. 2005/0096295 it is proposed to increase the sialic acid content of infant formula by including a novel CGMP ingredient having an enhanced concentration of sialic acid. This ingredient has a sialic acid content of more than 60 mg/g of peptide compared with 40 to 60 mg/g of peptide in naturally occurring CGMP. It may be produced either by fractionation using anion chromatography or by partial hydrolysis followed by fractionation using anion chromatography.

However, a need remains to provide other ingredients rich in sialic acid which can be used to enrich infant formula and other nutritional compositions in this important component.

SUMMARY OF THE INVENTION

The present invention provides an oligosaccharide ingredient comprising glycosylated amino acids and peptides of the general formula $R_n Sac_m$ where R is an amino acid residue, Sac is a monosaccharide selected from the group comprising N-acetyl-neuraminic acid, N-acetyl galactosamine and galactose, n has a value between 1 and 10 with the proviso that if n has the value 1 R is a threonine residue or a serine residue and if n has a value between 2 and 10 the peptide contains at least one threonine or serine residue, m has a value between 2 and 4 and at least 20 mol % of the ingredient is N-acetyl-neuraminic acid.

This ingredient is a new food grade ingredient rich in sialic acid which is suitable for addition to nutritional compositions such as infant formula to increase the sialic acid content of the composition.

The invention further extends to a process for producing an oligosaccharide ingredient comprising glycosylated amino acids and peptides of the general formula RnSacm where R is an amino acid residue, Sac is a monosaccharide selected from the group comprising N-acetyl-neuraminic acid, N-acetyl galactosamine and galactose, n has a value between 1 and 10 with the proviso that if n has the value 1 R is a threonine residue or a serine residue and if n has a value between 2 and 10 the peptide contains at least one threonine or serine residue, m has a value between 2 and 4 and at least 20 mol % of the ingredient is N-acetyl-neuraminic acid, comprising the steps of hydrolysing caseinoglycomacropeptide with an exoprotease and an endoprotease to obtain a mixture of free amino acids and peptides with a chain length between 2 and 10 and subjecting the hydrolysed mixture to nanofiltration so as to retain the fraction having a molecular weight between 1000 and 2000 Daltons.

The invention also extends to a food product comprising an oligosaccharide ingredient as described above. Optionally the food product is an infant food or formula, but the product may be any food or drink consumed by babies, infants or adults. Consumption of a food product containing such an oligosaccharide ingredient may improve incorporation of sialic acid into brain gangliosides and thus improve related neural functions such as neurotransmission.

DETAILED DESCRIPTION OF THE INVENTION

In the present specification, the following words are given a definition that must be taken into account when reading and interpreting the description, examples and claims.

"CGMP": caseino-glycomacropeptide, i.e. the glycomacropeptide that is cleaved from bovine κ-casein by the action of the enzyme rennin.

"Infant formula": foodstuff intended for the complete nutrition of infants during the first four to six months of life and for their partial nutrition thereafter. The term includes both starter and follow-on formulas.

"Sialic acid": N-acetylneuraminic acid.

The invention provides an oligosaccharide ingredient which comprises glycosylated amino acids and peptides of the general formula $R_n Sac_m$ where R is an amino acid residue, Sac is a monosaccharide selected from the group comprising N-acetyl-neuraminic acid, N-acetyl galactosamine and galactose, n has a value between 1 and 10 with the proviso that if n has the value 1 R is a threonine residue or a serine residue and if n has a value between 2 and 10 the peptide contains at least one threonine or serine residue, m has a value between 2 and 4 and at least 20 mol % of the ingredient is N-acetyl-neuraminic acid as well as infant or adult food products comprising such an oligosaccharide ingredient.

Preferably n has a value between 1 and 3 and m has a value of 3 or 4.

The ingredient contains at least 20 mol % sialic acid as part of a saccharide chain linked to the hydroxyl group of threonine or serine. The sialic acid may form part of the chain or may itself be a substituent of a monosaccharide unit in the chain. Thus, the oligosaccharide ingredient may contain the following monosaccharides:—

| Compound | mol % |
| --- | --- |
| N-acetyl galactosamine (GalNAc) | 10-25 |
| galactose (Gal) | 10-25 |
| N-acetyl-neuraminic acid (NeuAc) | 50-20 |

The oligosaccharide ingredient may contain from 15 to 50 mol % of a mixture of serine and/or threonine.

The oligosaccharide ingredient may contain the following glycosylated amino acids or peptides:—

NeuAc-α-2,3-Gal-β-1,3-(NeuAc-α-2,6-)-GalNAc-$R_n$
NeuAc-α-2,3-Gal-β-1,3-GalNAc-$R_n$
Gal-β-1,3-(NeuAc-α-2,6-)-GalNAc-$R_n$
Gal-β-1,3-GalNAc-$R_n$

The oligosaccharide ingredient of the invention may be produced by the hydrolysis of CGMP using an exoprotease and an endoprotease to obtain a mixture of free amino acids and peptides with a chain length between 2 and 10 and subjecting the hydrolysed mixture to nanofiltration so as to retain the fraction having a molecular weight between 1000 and 2000 Daltons.

CGGMP itself is a by-product of cheese-making in which whole milk is treated with the enzyme rennin to precipitate the casein. In this process, CGMP is cleaved from κ casein and remains in solution with the whey proteins. This product is known as sweet whey. The CGMP may be separated from the whey proteins by any process known in the art. A suitable process is described in European Patent No. 986312.

The hydrolysis may be carried out using any suitable combination of enzymes. One example of a commercially available enzyme system with exo- and endo-protease activity is the product sold as Flavourzyme® by the Novozymes division of Novo Nordisk.

The product of the hydrolysis process is a mixture of free amino acids, glycosylated threonine and serine, glycosylated peptides containing at least one threonine or serine residue and unglycosylated peptides, the peptides having a chain of 2 to 10 amino acid residues. This mixture is subject to nanofiltration to separate and retain the fraction having a molecular weight in the range from 1000 to 2000 Daltons. This fraction will comprise the oligosaccharide ingredient of the invention.

In a preferred aspect of the invention, the oligosaccharide ingredient described above is incorporated into a food product. In the context of the present invention, the term "food product" is intended to encompass any consumable matter. Hence, it may be a product intended for consumption by humans, in particular infant formula, follow-up formula, baby food such as infant cereals and the like. In particular, the oligosaccharide ingredient of the invention can be incorporated into infant formulas, growing up milks, and dehydrated milk or cereal mixtures.

The food product may be prepared in any suitable manner known in the art according to the type of product and the oligosaccharide ingredient of the invention may be added to the product at an appropriate stage in the manufacturing process. For example, an infant formula may be prepared by blending together the protein source, any carbohydrates other than lactose and the fat source in appropriate proportions. Emulsifiers may be added if desired. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger, e.g. a plate heat exchanger.

The liquid mixture may then be cooled to about 60° C. to about 85° C., for example by flash cooling. The liquid mixture may then be homogenised, for example in two stages at about 7 MPa to about 40 MPa in the first stage and about 2 MPa to about 14 MPa in the second stage. The homogenised mixture may then be further cooled to add any heat sensitive components such as vitamins and minerals. The pH and solids content of the homogenised mixture is conveniently standardised at this point.

The homogenised mixture is transferred to a suitable drying apparatus, such as a spray drier or freeze drier, and converted to powder. The powder should have a moisture content of less than about 5% by weight.

The oligosaccharide ingredient of the invention may be added directly to infant formula by dry mixing or, if in liquid for, at the blending stage discussed above. In both cases, it will be appreciated that addition of the ingredient entails the simultaneous addition of a quantity of amino-nitrogen and it may therefore be necessary to adjust the protein content of the infant formula or other product to which the ingredient is being added accordingly as will be evident to one skilled in the art. The permissible protein content and amino acid profile of infant formulas are specified in legislation such as European Commission Directive 91/321/EEC of 14 May 1991 and the person skilled in the art will easily be able to adjust the protein content and amino acid profile of the infant formula to take account of the additional amino-nitrogen introduced by the ingredient of the invention as well as the additional threonine and serine content.

The final concentration of the oligosaccharide ingredient in the baby or infant food product or formula may be from 0.2 to 4.0%, preferably 0.5 to 2.0% by weight of dry matter. However, these amounts should not be considered as limitative and should be adapted to the target population, for example based on the weight and age or health of the baby or infant. Preferably, the formula or feed containing the oligosaccharide ingredient of the invention is fed to the baby at every feed.

Although it is preferred to supplement food products specifically targeted towards infant or baby nutrition, it may be beneficial to supplement food products not specifically targeted, or targeted to the adult population. For example, the oligosaccharide ingredient of the invention can be incorporated into healthcare nutrition products and nutritional products for the elderly. Such food products may include milk, yoghurt, curd, cheese, fermented milks, milk-based fermented products, ice-creams, fermented cereal based products, or milk-based products, among others. In addition to the oligosaccharide ingredient of the invention, a food product such as an infant formula may comprise one or more further oligosaccharides which are added separately.

The invention will now be illustrated by reference to the following example.

Example 1

An example of the composition of an infant formula containing a oligosaccharide ingredient according to the present invention is given below.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| OS ingredient (g) | 0.15 | 1.0 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |

Example 2

50 g of caseinoglycomacropeptide (Biopure GMP, Davisco, USA) were dissolved at 10% (w/v) in 500 ml deionized water. The solution heated at 40° C. for 30 minutes while stirring gently and recirculated through a labscale tangential flow filtration system (Millipore, USA) with one Pellicon 1000 Da filter cassette (0.1 m$^2$) at a feed pressure of 1.2 bar and no retentate pressure.

Thereafter, an aminopeptidase from *Aspergillus oryzae* (Flavourzyme 1000 L containing 1000 aminopeptidase units per gram (LAPU/g), Novozymes, DK) was added at 3500 LAPU per 50 g protein. After about 1 hr, diafiltration was started by increasing the retentate pressure to 3 bars with a feed pressure of 3 bars. After 5 hrs the filtration was stopped and the retentate was collected. The retentate and the 7 permeate fractions that were collected during the process were lyophilized. Thereafter, dry matter (DM) and sialic acid content of each fraction was determined. Sialic acid content was measured after mild acid hydrolysis and labelling using the DMB (1,2-Diamino-4,5-methylenedioxybenzene dihydrochloride) method and analysis on an HPLC equipped with a Shodex C18 reverse phase column and a fluorescence detector using authentic NeuAc as external standards. Table 1 shows the mass balance and sialic acid content in starting material, permeate fractions and retentate.

TABLE 1

|  | mass (g) | NeuAc(% of DM) | yield (%) | enrichment |
|---|---|---|---|---|
| starting material | 50 | 7.5 | 100 | 1.00 |
| permeate 1 | 4.32 | 0.2 | 8.64 | 0.03 |
| permeate 2 | 3.1 | 0.2 | 6.2 | 0.02 |
| permeate 3 | 6.1 | 0.3 | 12.2 | 0.04 |
| permeate 4 | 4.29 | 1.4 | 8.58 | 0.18 |
| permeate 5 | 3.56 | 0.8 | 7.12 | 0.10 |
| permeate 6 | 2.8 | 0.4 | 5.6 | 0.05 |
| permeate 7 | 2.94 | 0.3 | 5.88 | 0.04 |
| retentate | 22.6 | 14.4 | 45.2 | 1.92 |

Galactose and N-acetyl-galactosamine content in the retentate were determined after acid hydrolysis using an HPAEC equipped with a Dionex CarboPac PA1 analytical column and a pulsed amperometry detector. Briefly, retentate was dissolved in water and tri-fluoroacetic acid was added to a final concentration of 2M. The solution was heated for 3 hr at 100° C., dried under a N-stream and redissolved with water. After filtration through a 22 um particle filter the sample was analysed. Quantification was done with authentic galactose and galactosamine (N-acetylgalactosamine becomes galactosamine during the acid treatment) as external standards. Threonine was quantified by HPLC after acid hydrolysis with 6N HCl.

The final dried retentate product contained 29.6 wt % (NeuAc)$_{2-3}$-Gal-GalNAc-Thr with the likely structure NeuAc-α-2,3-Gal-β-1,3-(NeuAc-α-2,6-)-GalNAc-threonine/peptide with 30 mol % sialic acid, 15 mol % galactose, 13 mol % N-acetyl galactosamine and 42 mol % threonine.

The invention claimed is:

1. An oligosaccharide ingredient comprising glycosylated amino acids and peptides of a general formula R$_n$Sac$_m$ where R is an amino acid residue, Sac is a monosaccharide selected from the group comprising N-acetyl-neuraminic acid, N-acetyl galactosamine and galactose, n has a value between 1 and 10 with the proviso that if n is 1 R is selected from the group consisting of a threonine residue and a serine residue and if n has a value between 2 and 10 the peptide contains at least one residue selected from the group consisting of threonine and serine residue, m has a value between 2 and 4, the oligosaccharide ingredient comprising 10 to 25 mol % N-acetyl galactosamine, 10 to 25 mol % galactose, 20 to 50 mol % N-acetyl-neuraminic acid and 15 to 50 mol % threonine or serine or a mixture thereof, the oligosaccharide ingredient comprising a glycosylated amino acid or peptide selected from the group consisting of NeuAc-α-2,3-Gal-β-1, 3-(NeuAc-α-2,6-)-GalNAc-R$_n$, NeuAc-α-2,3-Gal-β-1,3-GalNAc-R$_n$, Gal-β-1,3-(NeuAc-α-2,6-)-GalNAc-R$_n$, and Gal-β-1,3-GalNAc-R$_n$.

2. An oligosaccharide ingredient as claimed in claim 1 wherein n has a value between 1 and 3.

3. An oligosaccharide ingredient as claimed in claim 1 wherein m has a value of 2 or 3.

4. A food product comprising an oligosaccharide ingredient comprising glycosylated amino acids and peptides of a general formula R$_n$Sac$_m$ where R is an amino acid residue, Sac is a monosaccharide selected from the group comprising N-acetyl-neuraminic acid, N-acetyl galactosamine and galactose, n has a value between 1 and 10 with the proviso that if n is 1 R is selected from the group consisting of a threonine residue and a serine residue and if n has a value between 2 and 10 the peptide contains at least one residue selected from the group consisting of threonine and serine residue, m has a value between 2 and 4 and at least 20 mol % of the ingredient is N-acetyl-neuraminic acid, the oligosaccharide ingredient comprising 10 to 25 mol % N-acetyl galactosamine, 10 to 25 mol % galactose, 20 to 50 mol % N-acetyl-neuraminic acid and 15 to 50 mol % threonine or serine or a mixture thereof, the oligosaccharide ingredient comprising a glycosylated amino acid or peptide selected from the group consisting of NeuAc-α-2,3-Gal-β-1,3-(NeuAc-α-2,6-)-GalNAc-$R_n$, NeuAc-α-2,3-Gal-β-1,3-GalNAc-$R_n$, Gal-β-1,3-(NeuAc-α-2,6-)-GalNAc-$R_n$, and Gal-β-1,3-GalNAc-$R_n$.

5. A food product as claimed in claim 4 which is an infant formula.

6. A food product as claimed in claim 4 comprising from 0.2 to 4.0% by weight of the oligosaccharide ingredient.

7. An oligosaccharide ingredient as claimed in claim 1 wherein the oligosaccharide ingredient has at least one glycosylated amino acid selected from the group consisting of NeuAc-α-2,3-Gal-β-1,3-(NeuAc-α-2,6-)-GalNAc-$R_n$ and Gal-β-1,3-(NeuAc-α-2,6-)-GalNAc-$R_n$.

8. A food product as claimed in claim 4, wherein the oligosaccharide ingredient comprises at least one glycosylated amino acid selected from the group consisting of NeuAc-α-2,3-Gal-β-1,3-(NeuAc-α-2,6-)-GalNAc-$R_n$ and Gal-β-1,3-(NeuAc-α-2,6-)-GalNAc-$R_n$.

\* \* \* \* \*